United States Patent [19]

Donald et al.

[11] Patent Number: 5,179,087
[45] Date of Patent: Jan. 12, 1993

[54] MACROCYCLIC COMPOUNDS

[75] Inventors: David K. Donald; David N. Hardern; Martin E. Cooper, all of Leicestershire; Mark Furber, Derby, all of England

[73] Assignee: Fisons plc, England

[21] Appl. No.: 568,855

[22] Filed: Aug. 17, 1990

[30] Foreign Application Priority Data

Aug. 18, 1989 [GB] United Kingdom ............... 89/18886
Aug. 18, 1989 [GB] United Kingdom ............... 89/18929

[51] Int. Cl.$^5$ .................... A61K 31/33; C07D 225/08
[52] U.S. Cl. .................................... 514/183; 540/461
[58] Field of Search ................ 540/455, 461; 514/183

[56] References Cited

U.S. PATENT DOCUMENTS

| | | | |
|---|---|---|---|
| 4,275,149 | 6/1981 | Litman et al. ........................ | 435/177 |
| 4,894,366 | 1/1990 | Okuhara et al. ...................... | 514/63 |
| 4,929,611 | 5/1990 | Okuhara et al. ...................... | 514/411 |
| 4,956,352 | 9/1990 | Okahara et al. ...................... | 514/63 |

FOREIGN PATENT DOCUMENTS

| | | |
|---|---|---|
| EP184162 | 11/1986 | European Pat. Off. |
| 0349049 | 1/1990 | European Pat. Off. |
| 0349061 | 1/1990 | European Pat. Off. |
| 0353678 | 2/1990 | European Pat. Off. |
| 0356399 | 2/1990 | European Pat. Off. |
| WO8905304 | 6/1989 | PCT Int'l Appl. |

Primary Examiner—C. Warren Ivy
Assistant Examiner—Celia Chang
Attorney, Agent, or Firm—Marshall, O'Toole, Gerstein, Murray & Bicknell

[57] ABSTRACT

There are described compounds of formula I, wherein $R^1$ represents H or OH; $R^2$ represents H; in addition, $R^1$ and $R^2$ may together represent a second carbon-carbon bond between the carbon atoms to which they are attached; $R^3$ represents OH or OCH$_3$; X represents O or (H,OH); and Y represents O or N—OR$^4$, in which $R^4$ represents H or alkyl $C_{1-6}$; provided that when $R^1$ is OH, $R^2$ is H and X is O, then Y does not represent O.

Processes for their production and compositions containing them, eg. for use as immunosuppressive agents, are also described.

4 Claims, No Drawings

MACROCYCLIC COMPOUNDS

This invention relates to novel macrocyclic compounds, more particularly to novel macrocyclic immunosuppressive compounds, processes for their preparation, their use as medicaments, and compositions containing them.

European Patent Application 184162 (to Fujisawa Pharmaceuticals Co Ltd) discloses a number of macrocyclic compounds isolated from microorganisms belonging to the genus *Streptomyces*. The macrolides are numbered FR-900506, FR-900520, FR-900523 and FR-900525, and the preparation of some of their derivatives is also described.

International Patent Application WO 89/05304 (to Fisons plc), European Patent Application 353678 (to Fujisawa Pharmaceuticals Co Ltd), European Patent Applications 349049 and 349061 (to Merck & Co Inc) and European Patent Application 356399 (to Sandoz AG) also disclose a number of macrocyclic immunosuppressant compounds.

We have now found a novel group of compounds which possess certain advantageous properties over those disclosed previously.

Thus, according to the invention, we provide a compound of formula I,

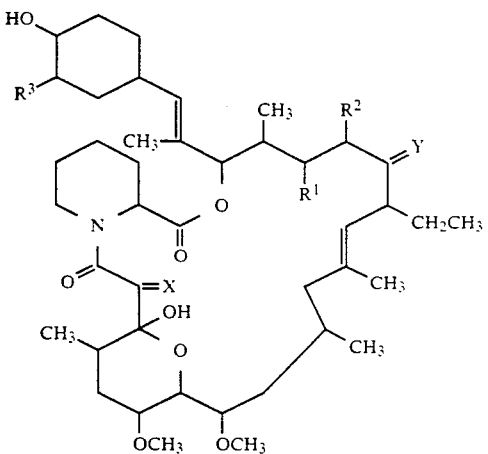

I wherein
$R^1$ represents H or OH;
$R^2$ represents H;
in addition, $R^1$ and $R^2$ may together represent a second carbon-carbon bond between the carbon atoms to which they are attached;
$R^3$ represents OH or $OCH_3$;
X represents O or (H,OH); and
Y represents O or $N-OR^4$, in which $R^4$ represents H or alkyl $C_{1-6}$;
provided that when $R^1$ is OH, $R^2$ is H and X is O, then Y does not represent O.

According to the invention, we also provide a process for the production of a compound of formula I, which comprises:
a) dehydration of a compound of formula I as defined above, but without proviso, in which $R^1$ represents OH and $R^2$ represents H, to give a corresponding compound of formula I in which $R^1$ and $R^2$ together represent a second carbon-carbon bond between the carbon atoms to which they are attached;
b) reduction of a compound of formula I as defined above in which $R^1$ and $R^2$ together represent a second carbon-carbon bond between the carbon atoms to which they are attached, to give a corresponding compound of formula I in which $R^1$ and $R^2$ each represent hydrogen;
c) reacting a compound of formula $NH_2-OR^4$, where $R^4$ is as defined above, or a derivative thereof, with a compound of formula I as defined above, but without proviso, in which Y represents O, to give a corresponding compound of formula I in which Y represents $N-OR4$; or d) reduction of a compound of formula I as defined above, but without proviso, in which X represents O, to give a corresponding compound of formula I in which X represents (H,OH).

In process (a), the dehydration may be carried out in a solvent which does not adversely affect the reaction (eg toluene), in the presence of a trace amount of acid (eg p-toluenesulphonic acid), at a temperature of from 50° to 100° C.

In process (b), the reduction may be carried out catalytically using hydrogen. Suitable catalysts include platinum catalysts (eg platinum black, platinum oxides), palladium catalysts (eg palladium oxides, palladium on charcoal), nickel catalysts (eg nickel oxide, Raney Nickel), and rhodium catalysts (eg rhodium on alumina). Suitable solvents are those which do not adversely affect the reaction, and include methanol, ethanol, ethyl acetate, dichloromethane and dimethylformamide. The reduction may be carried out at or around room temperature.

In process (c), derivatives of $NH_2-OR^4$ which may be mentioned include acid addition salts (eg hydrochlorides). Suitable solvents are those which do not adversely affect the reaction, and include methanol and ethanol. The reaction may be carried out at a temperature of from 50° to 100 C., eg the reflux temperature of the solvent employed, and preferably in the presence of pyridine.

In process (d), suitable reagents for the reduction include tri-$^n$butyltin hydride in a solvent which does not adversely affect the reaction (eg toluene) at a temperature of from 50° to 100° C., sodium borohydride, zinc in acetic acid at or around room temperature, sodium triacetoxyborohydride in acetic acid, L-Selectride (Registered Trade Mark) in tetrahydrofuran, or borane/$^t$butylamine complex in a solvent such as methanol or ethanol.

FR-900520 from EP 184162 and the compound of EP 349061 are useful starting materials for production of compounds of the present invention. Alternatively, the compound of the present invention, or starting materials therefor, may be produced by total synthesis (eg by modification of the method disclosed in European Patent Application 378318 to Merck & Co Inc).

The teaching of all the documents mentioned above is herein incorporated by reference.

The compounds of formula I may be isolated from their reaction mixtures using conventional techniques.

The compounds of formula I are useful because they possess pharmacological activity in animals; in particular they are useful because they possess immunosuppressive activity, eg in the tests set out in Tests A, B and C. Thus the compounds are indicated for use in the treatment or prevention of resistance to transplanted organs or tissues, such as kidney, heart, lung, bone marrow, skin, cornea, etc; and of autoimmune, inflammatory, proliferative and hyperproliferative diseases, and of cutaneous manifestations of immunologically-mediated diseases: for example rheumatoid arthritis, lupus erythematosus, systemic lupus erythematosus, Hashimoto's thyroiditis, multiple sclerosis, myasthenia gravis, type 1 diabetes, uveitis, nephrotic syndrome, psoriasis, atopical dermatitis, contact dermatitis and further eczematous dermatitides, seborrheic dermatitis, Lichen planus, Pemphigus, bullous Pemphigoid, Epidermolysis bullosa, urticaria, angioedemas, vasculitides, erythemas, cutaneous eosinophilias, Alopecia areata, etc.

The compounds of the invention are also indicated in the treatment of reversible obstructive airways disease.

Further, the compounds of the invention are indicated in the treatment of a disease selected from intestinal inflammations/allergies such as Coeliac disease, proctitis, eosinophilic gastroenteritis, mastocytosis, Crohn's disease and ulcerative colitis; and food related allergic diseases which have symptomatic manifestation remote from the gastro-intestinal tract, for example migraine, rhinitis and eczema.

The compounds of the invention are also indicated for use as antimicrobial agents, and thus may be used in the treatment of diseases caused by pathogenic microorganisms and the like.

We therefore provide the use of compounds of formula I as pharmaceuticals.

Further, we provide the use of a compound of formula I in the manufacture of a medicament for use as an immunosuppressive agent.

For the above-mentioned therapeutic uses the dosage administered will, of course, vary with the compound employed, the mode of administration, the treatment desired (eg topical, parenteral or oral) and the disease indicated. However, in general, satisfactory results are obtained when the compounds are administered at a daily dosage of from 0.001 to 20 mg per kg of animal body weight.

For man the indicated total daily dosage is in the range of from 0.01 mg to 1000 mg and preferably from 0.5 mg to 100 mg, which may be administered, for example twice weekly, or in divided doses from 1 to 6 times a day or in sustained release form. Thus unit dosage forms suitable for administration, eg oesophageally, comprise from 0.01 mg to 500 mg, and preferably 0.5 mg to 100 mg of the compound preferably admixed with a solid or liquid pharmaceutically acceptable diluent, carrier or adjuvant.

According to our invention we also provide a pharmaceutical composition comprising preferably less than 80%, and more preferably less than 50% by weight, of a compound of fomula I in combination with a pharmaceutically acceptable adjuvant, diluent or carrier. Examples of suitable adjuvants, diluents or carriers are: for tablets, capsules and dragees - microcrystalline cellulose, calcium phosphate, diatomaceous earth, a sugar such as lactose, dextrose or mannitol, talc, stearic acid, starch, sodium bicarbonate and/or gelatin; for suppositories - natural or hardened oils or waxes; and for inhalation compositions - coarse lactose. The compound of formula I preferably is in a form having a mass median diameter of from 0.01 to 10 μm. The compositions may also contain suitable preserving, stabilising and wetting agents, solubilisers (eg a water-soluble cellulose polymer such as hydroxypropyl methylcellulose, or a water-soluble glycol such as propylene glycol), sweetening and colouring agents and flavourings. The compositions may, if desired, be formulated in sustained release form.

For the treatment of reversible obstructive airways disease, we prefer the compound of formula I to be administered by inhalation to the lung, especially in the form of a powder.

According to a further aspect of the invention, there is provided a method of effecting immunosuppression which comprises administering a therapeutically effective amount of a compound of formula I, as defined above, to a patient.

The compounds of formula I have the advantage that they are less toxic, more efficacious, are longer acting, have a broader range of activity, are more potent, are more stable, produce fewer side effects, are more easily absorbed or have other useful pharmacological properties, than compounds previously used in the therapeutic fields mentioned above.

The compounds of formula I have a number of chiral centres and may exist in a variety of stereoisomers. The invention provides all optical and stereoisomers, as well as racemic mixtures. The isomers may be resolved or separated by conventional techniques.

However, the preferred stereochemistry of various chiral carbon atoms are shown in formula Ia,

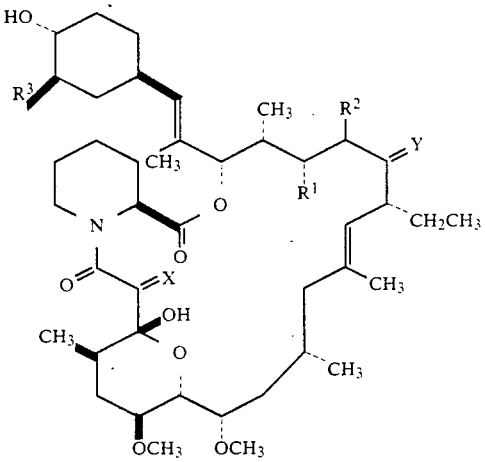

Ia wherein $R^1$ to $R^3$, X and Y are as first defined above.

Test A

Mixed Lymphocyte Reaction (MLR) I

The MLR test was performed in microtitre plates, with each well containing $5 \times 10^5$ C57BL/6 responder cells (H-$2^b$), $5 \times 10^5$ mitomycin C treated (25 μg/ml mitomycin C at 37° C. for 30 minutes and washed three times with RPMI 1640 medium) BALB/C stimulator cells (H-$2^d$) in 0.2ml RPMI 1640 medium supplemented with 10% fetal calf serum, 2 mM sodium hydrogen carbonate, penicillin (50 μg/ml) and streptomycin (50 μg/ml). The cells were incubated at 37° C. in a humidified atmosphere of 5% carbon dioxide and 95% of air for 68 hours and pulsed with $^3$H-thymidine (0.5 μCi) 4 hours before the cells were collected. The object compound of this invention was dissolved in ethanol and further diluted in RPMI 1640 medium and added to the cultures to give final concentrations of 0.1 μg/ml or less.

Test B

Mixed Lymphocyte Reaction (MLR) II

The MLR test was performed in 96-well microtitre plates with each well containing $3 \times 10^5$ cells from each of two responding donors in a final volume of 0.2 ml RPMI 1640 medium supplemented with 10% human serum, L-glutamine and penicillin/streptomycin. The compound under test was dissolved at 10 mg/ml in ethanol and further diluted in RPMI 1640. The cells were incubated at 37° C. in a humidified atmosphere at 5% carbon dioxide for 96 hours. 3H-thymidine (0.5 μCi) was added for the final 24 hours of the incubation to provide a measure of proliferation.

Test C

Graft versus Host Assay (GVH)

Spleen cells from DA and DAxLewis F1 hybrid rats were prepared at approximately $10^8$ cells/ml. 0.1 ml of these suspensions were injected into the rear footpads of DAxLewis F1 rats (left and right respectively). Recipient animals aere dosed with the compound under test, either orally or subcutaneously, on days 0-4. The assay is terminated on day 7 when the popliteal lymph nodes of the animals are removed and weighed. The increase in weight of the left node relative to the wieght of the right is a measure of the GVH response.

The invention is illustrated, but in no way limited by, the following Examples.

EXAMPLE 1

1,2,14-Trihydroxy-12-[2-(4-hydroxy-3-methoxycyclohexyl)-1-methylvinyl]-23,25-dimethoxy-17-ethyl-13,19,21,27-tetramethyl-11,28-dioxa-4-azatricyclo[22.3.1.0$^{4,9}$]octacos-18-ene-3,10,16-trione A solution of 1,14-dihydroxy-12-[2-(4-hydroxy-3-methoxycyclohexyl)-1-methylvinyl]-23,25-dimethoxy-17-ethyl-13,19,21,27-tetramethyl-11,28-dioxa-4-azatricyclo [22.3.1.0$^{4,9}$]octacos-18-ene-2,3,10,16-tetraone (FR-900520, EP 184162) (80 mg) and tri-$^n$butyltin hydride (0.2 ml) in toluene (5ml) was heated at 70° C. for 2 hours. The cooled reaction mixture was then evaporated in vacuo and the residue purified by column chromatograpghy on silica eluting with ethyl acetate to give the title compound as a foam (50 mg).

MS (FAB): 878 [M+Rb]$^+$; 816 [M+Na]$^+$; 794 [M+H]$^+$; 776 [M-OH]$^+$ $^{13}$C NMR (CDCl$_3$) δ: 214.5 (C16); 173.7 (C10); 169.5 (C3); 138.8 (C19); 131.9 (C29); 128.8 (C31); 122.8 (C18); 97.7 (C1); 84.2 (C34).

The title compound was also produced in the following manner:

A solution of 1,14-dihydroxy-12-[2-(4-hydroxy-3-methoxycyclohexyl)-1-methylvinyl]-23,25-dimethoxy-17-ethyl-13,19,21,27-tetramethyl-11,28-dioxa-4-azatricyclo [22 3.1.0$^{4,9}$]octacos-18-ene-2,3,10,16-tetraone (FR-900520, EP 184162) (80 mg) in acetic acid (10 ml) was treated with excess zinc dust (1 g) over 1 hour at room temperature. The reaction mixture was then filtered and evaporated in vacuo to a colourless oil. Chromatograghy on silica eluting with ethyl acetate then gave the diastereoisomers of the title compound (51 mg and 11 mg). The minor product was found to be identical to the product of the tri-$^n$butyltin hydride reduction described above.

MS (FAB): (major product) 878 [M+Rb]$^+$; 816 [M+Na]$^+$; 794 [M+H]$^+$; 776 [M-OH]$^+$ $^{13}$C NMR (CDCl$_3$) δ: (major product) 212.6 (C16); 173 (C10); 170.3 (C3); 140.2 (C19); 132.5 (C29); 130 (C31); 123.2 (C18); 99.3 (C1); 84.2 (C34).

EXAMPLE 2

1,14-Dihydroxy-12-2-(4-hydroxy-3-methoxycyclohexyl)-1-methylvinyl]23,25-dimethoxy-17-ethyl-13,19,21,27-tetramethyl-11,28-dioxa-4-azatricyclo[22.3.1.0$^{4,9}$]octacos-18-ene-2,3,10,16-tetraone C16-oxime A Solution of 1,14-dihydroxy-12-[2-(4-hydroxy-3-methoxycyclohexyl)-1-methylvinyl]-23,25-dimethoxy-17-ethyl-13,19,21,27-tetramethyl-11,28-dioxa-4-azatricyclo [22.3.1.0$^{4,9}$]octacos-18-ene-2,3,10,16-tetraone (FR-900520, EP 184162) (71mg), hydroxylamine hydrochloride (80 mg) and pyridine (0.2 ml) in dry ethanol (5 ml) was refluxed under an atmosphere of nitrogen for 2 hours. The reaction mixture was then cooled and poured into a mixture of dilute aqueous hydrochloric acid (1 N) and ethyl acetate. The ethyl acetate extract was washed with saturated aqueous sodium hydrogen carbonate solution, dried (MgSO$_4$), filtered and evaporated in vacuo to an oil. Chromatograghy on silica eluting with hexane/acetone [2:1] then gave the Z-oxime (7 mg) followed by the E-oxime (10 mg).

MS (FAB): (E- and Z-oximes) 891 [M+Rb]$^+$; 829 [M+Na]$^+$; 807 [M+H]$^+$; 789 [M-OH]$^+$.

$^{13}$C NMR (CDCl$_3$) δ: E-oxime 197.1 (C2); 169.3 (C10); 165.3 (C3); 162 (C16); 138.1 (C19); 132.7 (C29); 128 (C31); 125.8 (C18); 97.3 (C1); 84.2 (C34); 39.7 (C13); 39.1 (C5); 24.3 (C8); 21.4 (C6); 21 (C7); 12 (C44); 9.9 (C39). Z-oxime 169.5 (C2); 169 (C10); 165.3 (C3); 161.7 (C16); 138 (C19); 132.6 (C29); 128 (C31); 125.8 (C18); 97.3 (C1); 84.2 (C34); 9.5 (C39).

EXAMPLE 3

1-Hydroxy-12-[2-(4-hydroxy-3-methoxycyclohexyl)-1-methylvinyl]-23,25-dimethoxy-17-ethyl-13,19,21,27-tetramethyl-11,28-dioxa-4-azatricyclo22.3.1.0$^{4,9}$]-octacosa -14,18-diene-2,3,10,16-tetraone 1,14-Dihydroxy-12-[2-(4-hydroxy-3-methoxycyclohexyl)-1methylvinyl]-23,25-dimethoxy-17-ethyl-13,19,21,27-tetramethyl-11,28-dioxa-4-azatricyclo[22.3.1.0$^{4,9}$]octacos-14-ene-2,3,10,16-tetraone (FR-900520, EP 184162) (100 mg) and p-toluenesulphonic acid (2mg) were dissolved in dry toluene (20 ml) and heated for 2 hours at 100° C. under an atmosphere of nitrogen. Removal of solvent in vacuo and chromatography on silica eluting with hexane/acetone [2:1] gave the title compound as a foam (80 mg).

MS (FAB): 774.8 [M+H]$^+$; 796.85 [M+Na]$^+$; 858.71 [M+Rb]$^+$.

$^{13}$C NMR δ: (major rotamer) 201.15 (C16); 196.0 (C2); 169.2 (C10); 165.1 (C3); 147.8 (C15); 138.0 (C19); 123.82 (C18); 97.88 (C1); 84.05 (C34).

EXAMPLE 4

1-Hydroxy-12-[2-(4-hydroxy-3-methoxycyclohexyl)-1-methylvinyl]-23,25-dimethoxy-17-ethyl-13,19,21,27-tetramethyl-11,28-dioxa-4-azatricyclo22.3.1.0$^{4,91}$]octacos -18-ene-2,3,10,16-tetraone A sample of the title compound of Example 3 was dissolved in methanol (20 ml) and 10% Pd-on-carbon (10 mg) wa added. The mixture was stirred in an atmosphere of hydrogen for 1.5 hours at room temperature and pressure, and was then filtered through celite and evaporated to an oil in vacuo. Column chromatography on silica eluting with hexane/acetone [2:1] gave the title compound as a foam (50 mg).

MS (FAB): 776 [M+H]+; 798 [M+Na]+; 860 [M+Rb]+.

$^{13}$C NMR δ: (major rotamer) 212.34 (C16); 196.42 (C2); 169.38 (C10); 165.16 (C3); 138.9 (C19); 124.16 (C18); 97.41 (C1); 84.19 (C34).

We claim:

1. A compound of formula I,

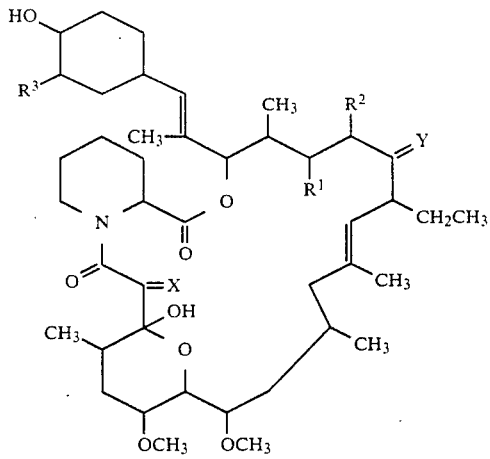

wherein
R$^1$ represents H or OH;
R$^2$ represents H;
in addition, R$^1$ and R$^2$ may together represent a second carbon-carbon bond between the carbon atoms to which they are attached;
R$^3$ represents OH or OCH$_3$;
X represents O or (H,OH); and
Y represents N-OR$^4$, in which R$^4$ represents H or alkyl C$_{1-6}$.

2. A compound of formula I as defined in claim 1, which is 1,14-dihydroxy-12-[2-(4-hydroxy-3-methoxycyclohexyl)-1-methylvinyl]-23,25-dimethoxy-17-ethyl-13,19,21,27-tetramethyl-11,28-dioxa-4-azatricyclo[22.3.1.0$^{4,9}$]octacos-18-ene-2,3,10,16-tetraone C16-oxime.

3. A pharmaceutical composition for achieving immunosuppression or for treatment of reversible obstructive airways disease, comprising an effective quantity of a compound of Formula I as defined in claim 1, in association with a pharmaceutically acceptable adjuvant, diluent, or carrier.

4. A method for treatment of diseases beneficially treated by administration of compounds having immunosuppressive activity in a patient in need of such treatment which comprises administering to such patient a therapeutically effective amount of a compound of formula I as defined in claim 1.

* * * * *